US00PP08061P

United States Patent [19]

Beck

[11] Patent Number: Plant 8,061

[45] Date of Patent: Dec. 15, 1992

[54] FERN PLANT NAMED 'VICTORIA'

[76] Inventor: George D. N. Beck, 6808 Overstreet Rd., Winderemere, Fla. 34786

[21] Appl. No.: 734,205

[22] Filed: Jul. 22, 1991

[51] Int. Cl.[5] ..... A01H 9/00
[52] U.S. Cl. ..... Plt./88.3
[58] Field of Search ..... Plt./88.3

[56] References Cited

U.S. PATENT DOCUMENTS

| | | | |
|---|---|---|---|
| P.P. 4,010 | 1/1977 | Biggers | Plt. 88.3 |
| P.P. 4,023 | 3/1977 | Miller | Plt. 88.3 |
| P.P. 4,253 | 5/1978 | Arnold | Plt. 88.3 |
| P.P. 4,257 | 5/1978 | McAllister | Plt. 88.3 |

OTHER PUBLICATIONS

L. H. Bailey; *The Standard Cyclopedia or Horticulture;* 1942, 1963; vol. I-A-E; pp. 413-415.
L. H. Bailey et al.; *Hortus Third;* 1976; pp. 120-121.
F. J. Cuittenden; *Dictionary of Gardening;* 1956; vol. I: A-Co; pp. 199-208.
T. H. Everett; *The New York Botanical Garden Illustrated Encyclopedia of Horticulture;* 1980; vol. I: A-Be; pp. 279-281.
A. B. Graf, D.Sc.; *Exotica International-Pictorial Encyclopedia of Exotic Plants from Tropical & Near-Tropic Regions;* Jun., 1985; vol. 1; pp. 1093-1097.
E. B. Copeland; *Fern Flora of the Philippines;* 1960; vol. 3; pp. 450-451.
A. B. Graf, D.Sc.; *Tropica-Color Cyclopedia of Exotic Plants and Trees from the Tropics and Subtropics;* May, 1978; pp. 442-445.
E. H. Walker; *Flora of Okinawa and the Southern Ryukyu Islands;* 1976; p. 110.
J. Ohwi; *Flora of Japan;* 1965; p. 96.

*Primary Examiner*—James R. Feyrer
*Attorney, Agent, or Firm*—James H. Beusse

[57] ABSTRACT

A new and distinct plant variety of the fern family that appeared as a mutation of the plant *Asplenium antiquum.* The present plant differs from the parent in having simple and foliaceous fronds with circinate venation and with leaves erecto-patent at the time of emergence becoming patulous with age, with a short stipe, and with mature blades being reflexed, entire, and regularly undulate along their margins.

4 Drawing Sheets

The invention relates to a new and distinct fern variety of the Aspleniaceae or spleenwort family which was discovered among spore propagated plants of *Asplenium antiquum,* which has been named "Victoria" by the inventor.

Plant varieties of the fern family commonly appear in the marketplace and many varieties represent species, hybrids or sports which are of unknown origin but which have characteristics that provide appeal to the public. Most are pinnately or multiply pinnately compound, grow on soil and have an elongated, sometimes decorative, fleshy or slender rhizomes. The new variety forming the subject matter of this application differs from "typical" ferns in that it forms basket-shaped rosettes of elongate undivided leaves which has led to the common name of bird's-nest ferns for the group.

The bird's-nest ferns, *Asplenium nidus,* including its varieties, have been popular foliage plants since introduction into cultivation at the Royal Botanical Gardens, Kew, in 1825. Their popularity is due to their large size, graceful form, attractive green leaves and ease of cultivation as house plants. *Asplenium antiquum* and the several varieties of *A. nidus* recognized in standard reference works (i.e., varieties *nidus, australasicum,* and *musaefolium*) have leaf margins that are entire to repand or somewhat irregularly wavy undulate. The *A. nidus* variety *plicatum* has a blade that is distinctly transversely plicate from the midrib to the margin. The *A. nidus* variety *phyllitidus* is repand and irregularly undulate at the margin. The *A. nidus* variety *crispaefolium* is irregularly undulate at the margin with strong tendencies for the leaves to twist or be otherwise contorted. The species *antiquum* was first described by Makino in 1929 from the southern Japanese archipelago and the species has been recognized as a distinct taxon by most fern references since. Plants of typical *A. antiquum* are commonly somewhat smaller than *A. nidus* and have fronds generally lanceolate rather than oblanceolate or spathulate as in *A. nidus.* Margins of fronds of *A. antiquum* are entire and with tendencies toward an irregular weak undulation.

The new invention was grown from a planting of spores of *Asplenium antiquum.* The developing leafy sporophyte plant was cultivated in Metro-mix 500 medium comprised of Canadian sphagnum peat, vermiculate, bark ash, composted pine bark, and washed granite sand. The hybrid plant was selected and asexually reproduced by tissue culture in a laboratory and grown to market size at the inventor's nursery located near Windermere, Fla.

The variety reproduces true from spores as well as by asexual reproduction and the accompanying drawings serve, by color photographic means, to illustrate the new variety.

One color photograph shows a 10 month old specimen of the new variety which was grown in a plastic container under nursery conditions contemplated hereinafter.

Another color photograph shows the rosette of fronds as seen from a high angle and the close up of the apex shows the circinate venation and the scaly nature of the stem and lower leaves. Features of a 15 month old specimen are shown in a close up of the adaxial surface of the base of a frond with typical costal and blade scales along with a single stem scale at the site of the cut. A longitudinal cut through the stem of a 15 month old specimen shows its fleshy nature, scales and an emerging frond.

Another photograph shows a portion of the root mass of a 15 month old plant grown in a 6 inch pot and an abaxial view of fronds. A close up of the abaxial surface of a 15 month old frond shows immature typical linear sori.

Through successive propagations as described, it has been ascertained that specimens of the new plant variety retain their distinctive characteristics. The following is a detailed description of the new plant variety at the age of 10 months past tissue culture, unless otherwise noted, with colors and hues, unless otherwise clearly indicated by the text, being named in accord with the ISCC-NBS Method of Designating Colors (U.S. Department of Commerce, National Bureau of Standards, Special Publication 440 issued December, 1976), the named colors being interpreted from color notations derived by comparison with color specimens in the Munsell Book of Color, Matte Finish Collection, published by Munsell Color, Macbeth, A Division of Kollmorgen Corporation, 2441 North Calvert Street, Baltimore, Md. 21218, dated March 1979.

DETAILED PLANT DESCRIPTION

Name: *Asplenium antiquum* Makino (cv) "Victoria".

Parentage: *Asplenium antiquum* mutation originating from propagation by spores.

Classification:

I. *Botanic.—family.*—Aspleniacea or spleenwort (Fern Family). Genus: Asplenium. Species: *antiquum.*

II. Commercial: Fern foliage plant.

Form: Epiphytic of terrestrial (in cultivation), with erecto-patent leaves from a rosette surrounding a large flattened bud terminating a short, terete, erect stem.

Stems:

A. *General.*—Short and upright with brown, membranous, toothed scales and an adventitious root system.

B. *Stem texture.*—Scurfy and fleshy. 1) Stem scales: a) General: Closely imbricate and somewhat contorted giving the stem a scurfy appearance. b) Size: (1) Length: Usually between 5.0 and 10.0 mm. (2) Width (Maximum): Usually between 1.5 and 3.0 mm. c) Shape: Generally ovate lanceolate, lanceolate, and/or linear lanceolate. d) Margin: Generally irregularly dentate or ciliate-dentate by stalked slime cells. e) Aerolation: Generally rectangular to rhombic in somewhat sinuous rows and with secondary walls pegged towards the lumen on lateral walls. f) Color: (1) General: Distal blade area with a color that is dominated by a reddish brown hue that merges proximally with color in a transition zone that is usually dominated by orange and/or orange yellow hue and in turn merges into basal area. The basal area is hyaline with a yellow hue. (2) Distal blade area: Commonly moderate reddish brown (7.5R3/4) (7.5R3/6) (10R3/4) in the outer field and moderate orange (near 5YR6/10), strong orange (near 5YR6/10) (5YR6/12) (5YR7/12), dark orange yellow (near 7.5YR6/10), deep orange yellow (near 7.5YR6/10), moderate orange yellow (near 7.5YR7/10) (7.5YR7/12) (10YR7/12) (near 10YR8/10), light orange yellow (near 10YR8/10), brilliant orange yellow (near 10YR8/10), vivid yellow (2.5Y8/12), brilliant yellow (near 2.5Y8/10), and strong yellow (near 2.5Y8.10) in the transition zone. (3) Basal blade area: Commonly white (near 10YR9/1) and yellowish white (near 10YR9/1) (2.5Y9/2). 2) Stem tissues: Parenchymatous with separate vascular traces.

C. *Stem size.*—1) Length: Usually between 15 mm and 25 mm at age of 10 months past tissue culture. 2) Diameter (Maximum): Usually between 15 mm and 30 mm at age of 10 months past tissue culture.

D. *Stem shape.*—Terete with a tendency to be broader above and with the apical meristem in a shallow depression.

Roots:

A. *General.*—Adventitious, fibrous, woolly, usually subterranean in cultivation, freely branched and with a color dominated by reddish brown and/or brown hues.

B. *Size.*—1) Length: Usually between 15 and 40 cm. 2) Diameter: Usually between 0.5 mm and 1.5 mm including indumentum.

C. *Color.*—Commonly dark grayish reddish brown (near 2.5YR2.5/2), grayish reddish brown (near 2.5YR2.5/2) (2.5YR3/2), grayish brown (5YR3/2), moderate brown (5YR4/4) (7.5YR4/4), and/or strong brown (5YR4/6) (7.5YR4/6).

Fronds:

A. *General.*—Simple and foliaceous with circinate venation and with leaves erecto-patent at the time of emergence becoming patulous with age, with a short stipe, and with matured blades being reflexed.

B. *Arrangement.*—Alternate and rosulate.

C. *Shape.*—Generally varies from narrowly lanceolate or narrowly eliptic lanceolate, to linear lanceolate with a broadly cuneate base with tendencies to become decurrent to the short stipe.

D. *Size.*—1) Length (including stipe): Usually between 3 and 45 cm for the lowermost whorl of fronds at the age of 10 months, and usually between 35 cm and 55 cm for the longest fronds in the rosette at the age of 10 months past tissue culture. 2) Width (maximum): Usually between 1 cm and 7.5 cm for the lowermost whorl of fronds and usually between 2.5 cm and 7.5 cm for the longest fronds in the rosette at the age of 10 months.

E. *Stipe.*—1) General: Herbaceous and fleshy. 2) Texture: Generally glabrous with a few scattered membranous scales of reddish brown hues. (a) Scales: (1) General: Scattered, membranous and attached at the proximal end. (b) Size: (1) Length: Usually 2 mm to 5 mm when fully expanded. (2) Width: Usually 0.5 mm to 2 mm when fully expanded. (c) Shape: Commonly linear to linear lanceolate, often contorted, sessile from a proximal attachment, and irregularly toothed along the margin. (d) Color of scales: Commonly moderate reddish brown (7.5R3/4) (7.5R3/6) (10R3/4), grayish reddish brown (near 10R2.5/2) (7.5R3/2) (10R4/2), dark grayish reddish brown near (10R2.5/2) and/or grayish red (7.5R4/2). 3) Shape of Stipe: Generally depressed obovate to transversely elliptic in cross-section. 4) Size: (a) Length: Usually between 2 mm and 14 mm when measured from insertion to the base of the blade. (b) Diameter: Usually between 3 mm and 7 in the longest direction and between 1.5 mm and 4 mm in the shorter direction. 5) Color: Commonly dark reddish gray (near 5R2.5/1) (near 5R3/1) (near 10R2.5/1), dark reddish red (near 5R2.5/1) (5R2.5/2), dark gray (near 5R3/1), grayish reddish brown (near 7.5R5/2) (near 10R2.5/2), and/or dark grayish reddish brown (near 7.5R2.5/2) (near 10R2.5/1) (near 10R2.5/2).

F. *Costa.*—1) General: Herbaceous and generally flexible and fleshy during each maturity and hardening with age being an extension of the stipe into the simple blade and extending to the leaf tip. 2) Texture: Glabrous with widely scattered small linear lanceolate scales on both surfaces of the proximal half of the leaf. 3) Shape: Generally tapering distally from the stipe and depressed obovate to transversely elliptic in cross-section. 4) Color: (a) General: distal end surface color dominated by olive, olive green, greenish yellow, yellow green and/or yellowish green hues merging in a median transition zone toward the proximal end with its surface color being dominated by red, reddish brown, brown, and/or reddish orange. (b) Apices (adaxial and abaxial): Commonly light olive (10Y5/6), dark greenish yellow (near 10Y6/8), deep greenish yellow (near 10Y6/8), moderate yellow green (2.5GY5/6) (5GY5/6) (7.5GY5/6), strong yellow green (2.5GY6/8) (2.5GY7/8) (2.5GY7/10) (5GY5/8) (5GY6/8)(5GY7/8) (7.5GY5/8) with older (lower) leaves tending toward moderate greenish yellow (near 10Y7/8) and/or strong greenish yellow (near 10Y7/8) with age. (c) Median transitional zone (adaxial): Commonly moderate yellow green (2.5GY5/6) (5GY5/4) (5GY5/6) (5GY6/6) (7.5GY5/6), strong yellow green (2.5GY6/8) (5GY5/4), moderate olive green (5GY4/4) (7.5GY4/4), moderate yellowish green (10GY5/6) and/or dark yellowish green 10GY4/4). (d) Median transitional zone (abaxial): Commonly moderate yellow green (2.5GY5/4) (2.5GY5/6) (5GY5/4) (5GY5/6) (5GY6/4) (5GY6/6) (7.5GY5/4) (7.5GY5/6), strong yellow green (5GY5/8), moderate olive green (5GY4/4), and/or moderate yellowish green (10GY5/4) (10GY5/6) in the distal portions merging proximally into a middle band which is commonly dark grayish red (2.5R2.5/2) (2.5R3/2) (5R2.5/2) (5R3/2) (near 5R2.5/1), dark grayish reddish brown (7.5R2.5/2) (near 10R2.5/1) (near 10R2.5/2), grayish reddish brown (7.5R3/2) near 10R2.5/2) (10R3/2), dark reddish gray (near 10R2.5/1) (near 5R2.5/1), moderate reddish brown (7.5R3/4) (10R4/4) (10R4/6), dark reddish orange (10R4/8), grayish reddish orange (10R5/6), and/or strong brown (2.5YR4/6) (2.5YR4/8). (e) Proximal end (adaxial and abaxial): Commonly dark grayish red (2.5R2.5/2) (near 2.5R2.5/3) (near 5R2.5/1) )5R2.5/2) (5R3/2), dark reddish gray (near 5R2.5/1) (5R3/1) (near 10R2.5/1), grayish reddish brown (near 7.5R2.5/2) (7.5R3/1) (near 10R2.5/2) (10R3/2), dark red (near 2.5R2.5/3) (5R3/4), moderate reddish brown (10R3/4), dark grayish brown (near 7.5R2.5/2), and/or dark grayish reddish brown (near 10R2.5/1) (near 10R2.5/2).

G. Blade: 1) General: Chartaceous, simple and pinnately veined from the costa. 2) Texture: Glabrous distally but commonly with scattered small scales proximally, comparable in size, shape, and color to those on the costa. 3) Shape: Generally varies from narrowly lanceolate, elliptic lanceolate to linear lanceolate with a narrowly acuminate tip and a broadly rounded to cuneate base with tendencies to be short decurrent to the stipe. 4) Margins: Entire and regularly undulate with a horizontal amplitude (crest to crest), commonly between 1.5 cm and 3 cm at mid-blade and with a vertical amplitude (crest to trough) commonly between 0.5 cm and 1.5 cm mid-blade. 5) Size: a) Length: Usually between 2.8 cm and 40 cm for the lowermost whorl of fronds and usually between 30 cm and 50 cm for the largest fronds of the rosette at the age of 10 months past tissue culture. b) Width (maximum): Usually between 1 cm and 7.5 cm for the lowermost whorl of fronds and usually between 2.5 cm and 7.5 cm for the largest fronds in the rosette at the age of 10 months past tissue culture. 6) Color: a) Upper epidermis (basal whorl): Commonly dark greenish yellow (near 10Y6/8), deep greenish yellow (near 10Y6/8), strong greenish yellow (near 10Y7.8), moderate greenish yellow (near 10Y6/8), strong yellow green (2.5GY6/8) (2.5GY7/10) (5GY5/8), and/or moderate yellow green (2.5GY7/4) (2.5GY6/6) (2.5GY7/6) (5GY5/4) (5GY5/6) (5GY6/6) (5GY6/4). b) Lower epidermis (basal whorl): Commonly grayish greenish yellow (near 10Y8.4), pale greenish yellow (near 10Y8/4), light greenish yellow (near 10Y8/6), moderate greenish yellow (near 10Y8.6) (10Y7/6), light yellow green (2.5GY8/6), moderate yellow green (2.5GY7/6) (5GY5/4) (5GY5/6) (5GY6/6) (5 GY7/6) (7.5GY6/6) (7.5GY7/6) and/or strong yellow green (5GY6/8). c) Upper epidermis (largest whorl): Commonly moderate olive green (5GY4/4), moderate yellow green (5GY5/6) (5GY6/6) (5GY7/6) (7.5GY5/4) (7.5GY5/6), and/or strong yellow green (5GY5/8) (5GY6/8) (5GY7/8) (7.5GY5/8). d) Lower epidermis (largest whorl): Commonly strong yellow green (5GY5/8) and/or moderate yellow green (2.5GY5/6) (5GY5/4) (5GY5/6) (5GY6/4) (5GY6/6) (7.5GY5/4) (7.5GY5/6) (7.5GY6/4) (7.5GY6/6). 7) Sori: None in plants at the age of 10 months past tissue culture. Linear in the distal portion of the leaf and parallel to the veins on the abaxial side of some fronds at the age of 15 months past tissue culture.

The above description is based upon observations made during the month of February of well fertilized plants about 10 months old, unless otherwise specifically stated, (from tissue culture) and which were grown under approximately 60 percent shaded conditions in the Windermere, Fla. area.

I claim:

1. The new and distinct plant variety of the fern family substantialy as herein described and illustrated and characterized by a growth habit which provides specimens that have simple, costate fronds that grow in a rosette arrangement, and which, in comparision to specimens of the parent variety, exhibit a strongly and regularly undulate margin that contrasts with the repand margins of the parent.

* * * * *

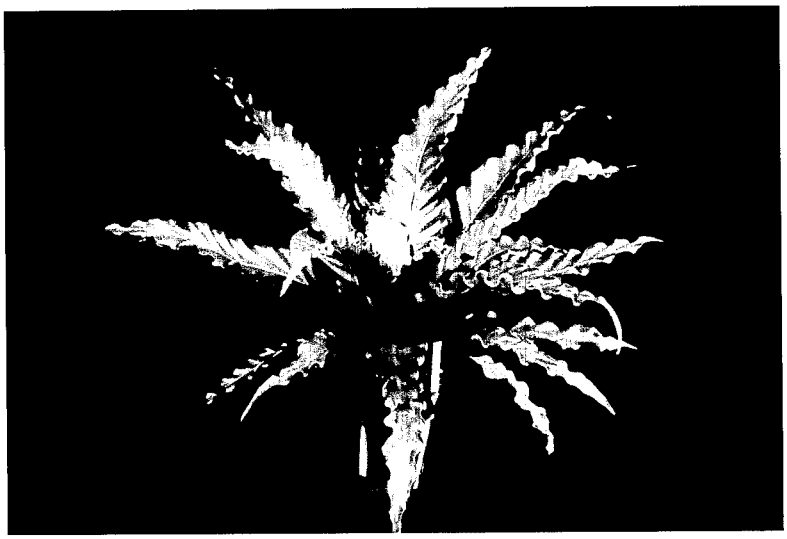
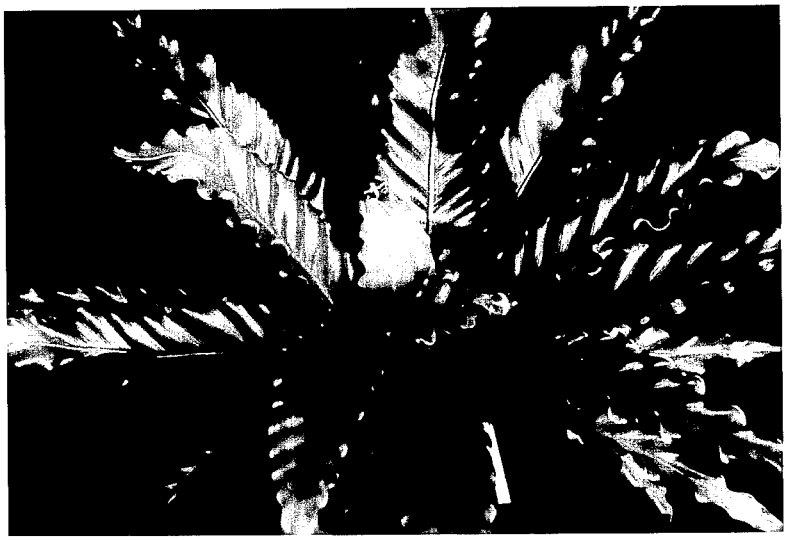

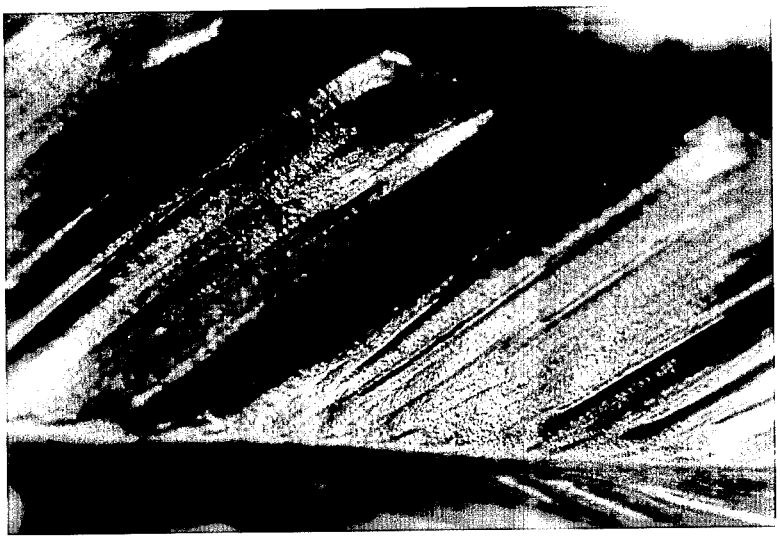
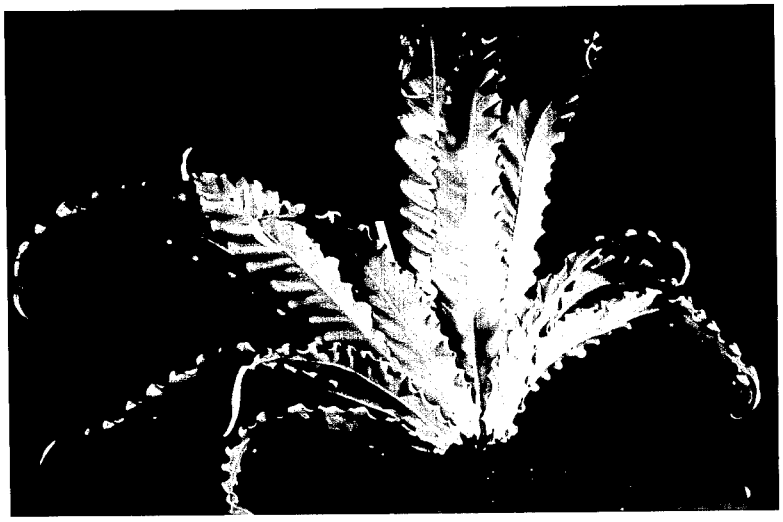

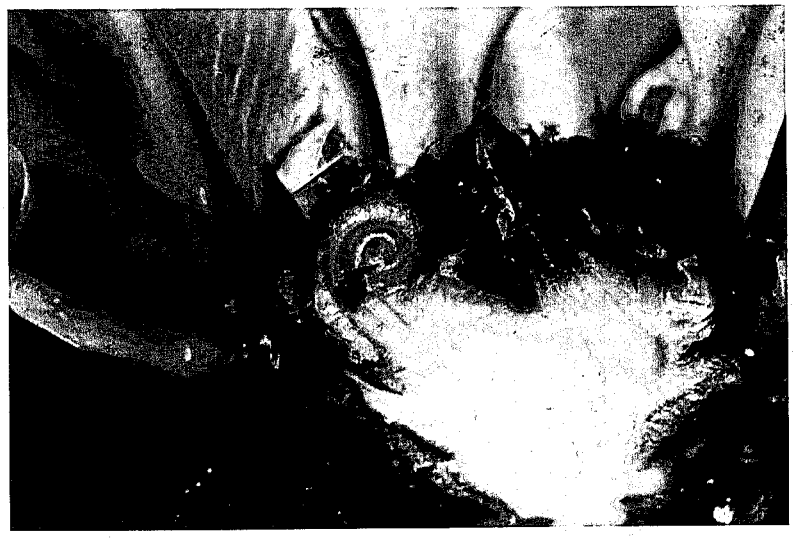

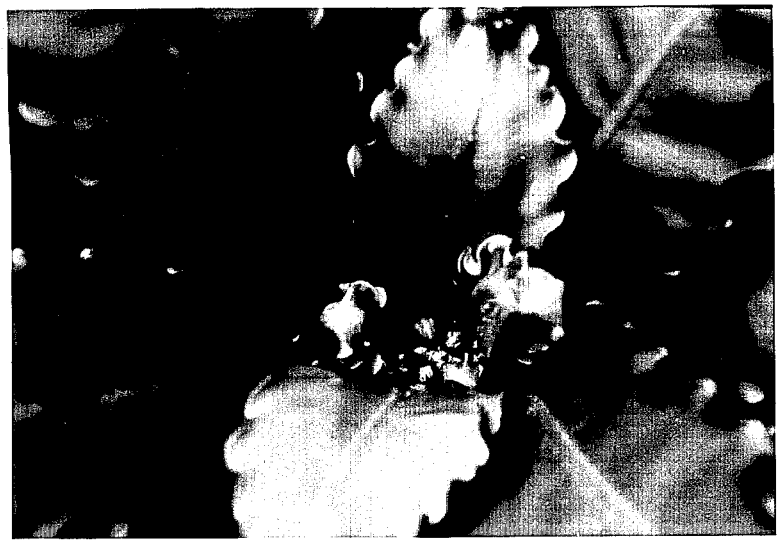
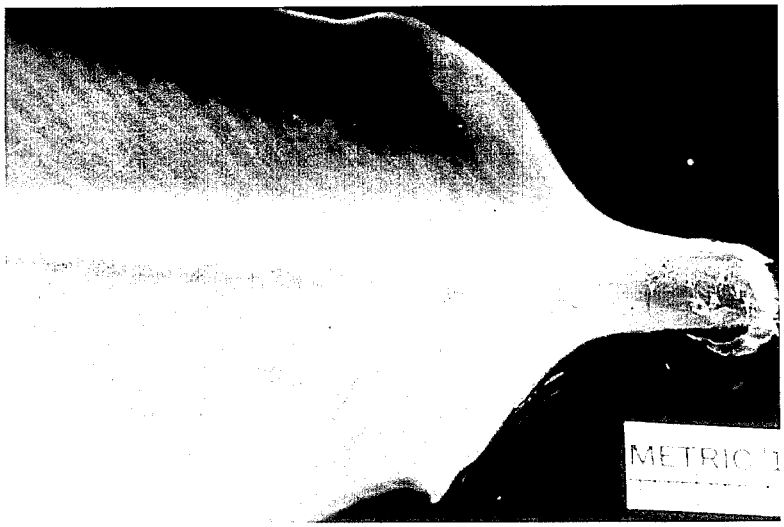
METRIC